(12) United States Patent
Ouchi et al.

(10) Patent No.: US 12,343,150 B2
(45) Date of Patent: Jul. 1, 2025

(54) ELECTRODE

(71) Applicant: Murata Manufacturing Co., Ltd., Nagaokakyo (JP)

(72) Inventors: Tomoki Ouchi, Nagaokakyo (JP);
Yoichi Moriya, Nagaokakyo (JP);
Kahori Takatsuki, Nagaokakyo (JP);
Koji Tanaka, Nagaokakyo (JP);
Katsuhisa Higashiyama, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 185 days.

(21) Appl. No.: 18/173,406

(22) Filed: Feb. 23, 2023

(65) Prior Publication Data
US 2023/0270365 A1    Aug. 31, 2023

(30) Foreign Application Priority Data

Feb. 25, 2022  (JP) .................................. 2022-028410
Dec. 13, 2022  (JP) .................................. 2022-198816

(51) Int. Cl.
*H01B 7/00* (2006.01)
*A61B 5/263* (2021.01)
*A61B 5/273* (2021.01)
*H01B 1/02* (2006.01)

(52) U.S. Cl.
CPC .............. *A61B 5/273* (2021.01); *A61B 5/263* (2021.01); *H01B 1/02* (2013.01); *H01B 7/0027* (2013.01)

(58) Field of Classification Search
CPC ........... A61B 5/273; A61B 5/263; A61B 5/27; A61B 2562/0209; H01B 7/0027; H01B 1/02; A61N 1/04; H05K 1/11; H05K 1/111
See application file for complete search history.

(56) References Cited

U.S. PATENT DOCUMENTS

| | | | |
|---|---|---|---|
| 10,143,835 B2 | 12/2018 | Ejiri et al. | |
| 2022/0141963 A1* | 5/2022 | Feng | H05K 3/16 29/849 |
| 2022/0167497 A1* | 5/2022 | Fukao | H05K 1/118 |
| 2022/0221354 A1* | 7/2022 | Xiao | A61B 5/1126 |

FOREIGN PATENT DOCUMENTS

JP          2018023568 A       2/2018

* cited by examiner

*Primary Examiner* — Roshn K Varghese
(74) *Attorney, Agent, or Firm* — ArentFox Schiff LLP

(57) ABSTRACT

An elastically deformable electrode that includes a plurality of electrode elements spaced from each other, and a liquid wire which is a liquid conductor configured to electrically connect the plurality of electrode elements. The electrode may also include a solid wire sealing the liquid wire, and an insulator between the solid wire and the plurality of electrode elements.

19 Claims, 14 Drawing Sheets

FIG. 12A
FIG. 12B
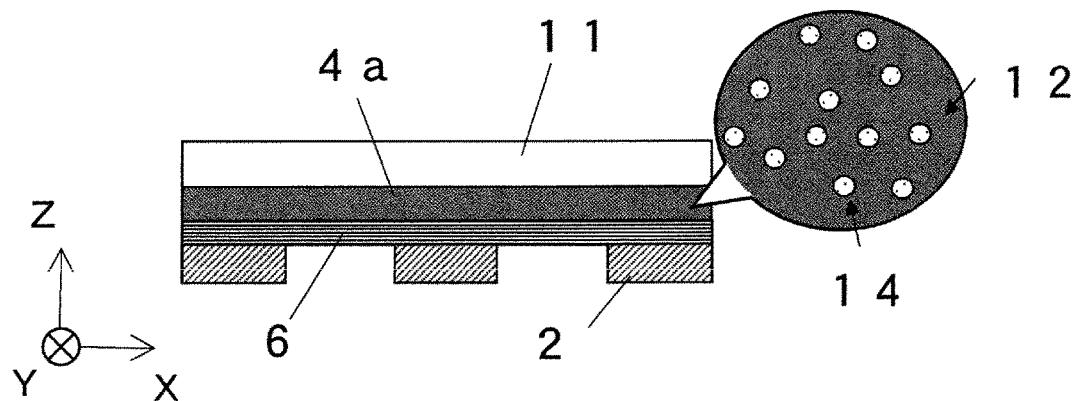
FIG. 13
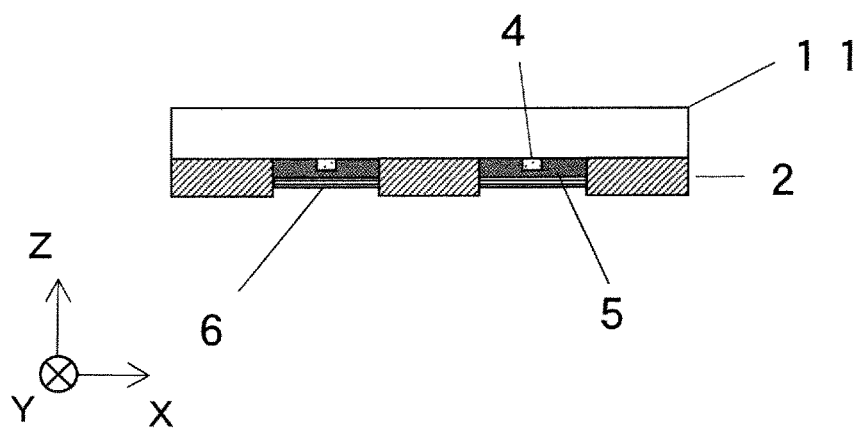

ELECTRODE

CROSS REFERENCE TO RELATED APPLICATIONS

The present application claims priority to Japanese Patent Application No. 2022-028410, filed Feb. 25, 2022, and Japanese Patent Application No. 2022-198816, filed Dec. 13, 2022, the entire contents of each of which are incorporated herein by reference.

BACKGROUND OF THE INVENTION

Field of the Invention

The present invention relates to a biomedical electrode or an electrode used on a changing surface of a non-living object.

Description of the Related Art

Japanese Unexamined Patent Application Publication No. 2018-23568 describes a biomedical electrode that includes an electrode sheet with many electrode elements spaced from each other, and a conductive cloth disposed on the electrode sheet. The electrode sheet is a stretchable and flexible mesh sheet that includes stretchable linear members configured to couple adjacent ones of the electrode elements. With the stretchable and flexible mesh sheet serving as the electrode sheet, this backboard electrode can suitably follow surface changes of a living body while maintaining a contact area and close contact with the living body.

SUMMARY OF THE INVENTION

The biomedical electrode described in Japanese Unexamined Patent Application Publication No. 2018-23568 includes a fibrous conductive member. This results in generation of noise which is probably caused by changes in resistance associated with stretching of the fibrous conductive member.

An object of the present invention is to provide a biomedical electrode or an electrode used on a changing surface of a non-living object, and specifically to provide an electrode configured to suppress noise caused by changes in resistance associated with expansion and contraction.

An electrode according to the present invention is an elastically deformable electrode. The electrode includes a plurality of electrode elements spaced from each other, and a liquid wire which is a liquid conductor configured to electrically connect the plurality of electrode elements.

The electrode according to the present invention includes a liquid wire between electrode elements. This can suppress noise caused by changes in resistance associated with expansion and contraction.

BRIEF DESCRIPTION OF THE DRAWINGS

FIG. 12A is a schematic cross-sectional view illustrating a cross-sectional structure of an electrode according to Embodiment 6, and FIG. 12B is an enlarged cross-sectional view illustrating a detailed cross-sectional structure of a liquid wire illustrated in FIG. 12A;

FIG. 13 is a schematic cross-sectional view illustrating a cross-sectional structure of an electrode according to Embodiment 7;

DETAILED DESCRIPTION OF THE PREFERRED EMBODIMENTS

Figure 1:
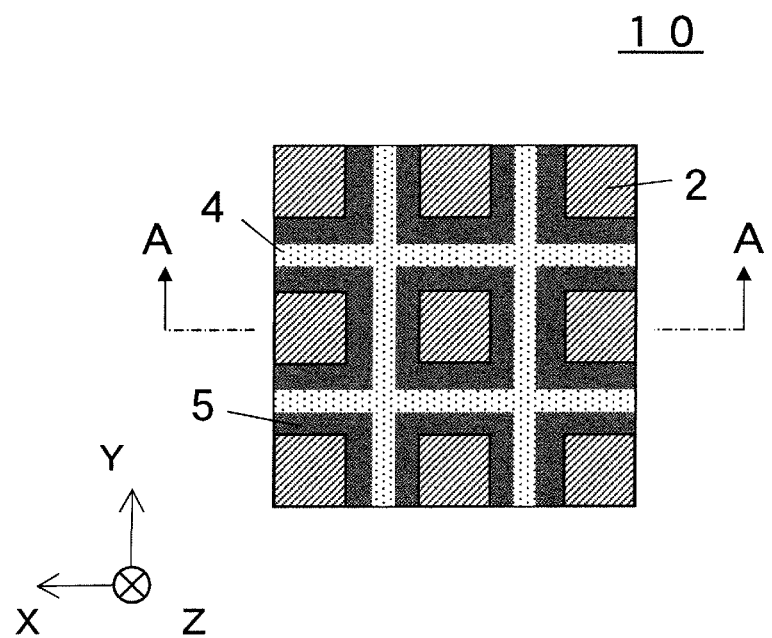
FIG. 1 is a transparent bottom view of a planar arrangement, illustrating in a visible manner a liquid wire of an electrode according to Embodiment 1.

An electrode according to Aspect 1 is an elastically deformable electrode. The electrode includes a plurality of electrode elements spaced from each other, and a liquid wire which is a liquid conductor electrically connecting the plurality of electrode elements.

According to Aspect 2, in the electrode of Aspect 1, the plurality of electrode elements may be disposed to form a first surface of the electrode.

According to Aspect 3, in the electrode of Aspect 1 or 2, when the electrode is elastically deformed in such a way that a first distance between two of the plurality of electrode elements is twice a second distance between the two of the plurality of electrodes when not elastically deformed, a first resistance at the first distance may be less than or equal to 50 times a second resistance at the second distance.

According to Aspect 4, in the electrode of Aspect 1 or 2, when the electrode is elastically deformed in such a way that a first distance between two of the plurality of electrode elements is twice a second distance between the two of the plurality of electrodes when not elastically deformed, a first resistance of the liquid wire connecting the two electrode elements at the first distance may be less than or equal to 10 times a second resistance of the liquid wire connecting the two electrode elements at the second distance.

According to Aspect 5, in the electrode of any one of Aspects 1 to 4, the liquid wire may contain a metal which is liquid at ordinary temperature.

According to Aspect 6, in the electrode of any one of Aspects 1 to 5, the liquid wire may contain a metal containing greater than or equal to 60% by weight of gallium.

According to Aspect 7, in the electrode of Aspect 6, the liquid wire may contain a metal containing less than or equal to 40% by weight of indium.

According to Aspect 8, in the electrode of any one of Aspects 1 to 7, the liquid wire may be disposed to extend from a first toward a second of two adjacent electrodes of the plurality of electrode elements.

According to Aspect 9, in the electrode of any one of Aspects 1 to 8, the liquid wire may have a resin configured to seal a perimeter of the liquid wire.

According to Aspect 10, in the electrode of any one of Aspects 1 to 9, the electrode may further include a substrate disposed so as to support the plurality of electrode elements.

Electrodes according to embodiments will now be described with reference to the accompanying drawings. In the drawings, substantially the same components are denoted by the same reference numerals.

Embodiment 1

Figure 2:
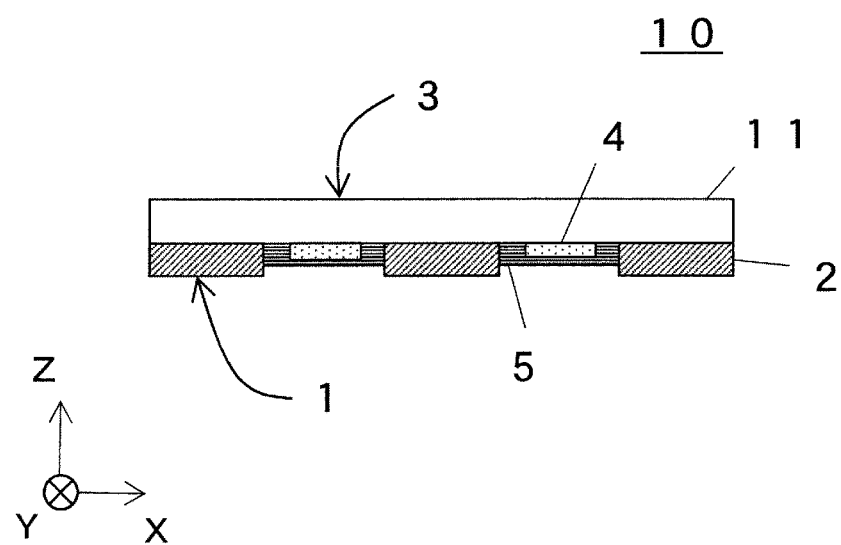
FIG. 2 is a schematic cross-sectional view of a cross-sectional structure viewed in direction A-A of FIG. 1.

FIG. 1 is a transparent bottom view of a planar arrangement, illustrating in a visible manner a liquid wire 4 of an electrode 10 according to Embodiment 1. FIG. 2 is a schematic cross-sectional view of a cross-sectional structure viewed in direction A-A of FIG. 1. In FIG. 1 and FIG. 2, for convenience, a plane facing a measured surface of an object to be measured is defined as an XY plane, and a direction perpendicular to the XY plane is defined as a Z direction.

As illustrated in FIG. 1, the electrode 10 according to Embodiment 1 includes a plurality of electrode elements 2 spaced from each other and disposed to form a first surface 1, and a liquid wire 4 which is a liquid conductor configured to electrically connect the electrode elements 2. The electrode 10 further includes a solid wire 5 configured to seal the liquid wire 4, and a planar substrate 11 configured to support the plurality of electrode elements 2 and the liquid wire 4. In the electrode 10, the liquid wire 4 and the solid wire 5 between adjacent ones of the electrode elements 2 are configured to electrically connect the electrode elements 2 in the in-plane direction.

When a surface shape of the object to be measured changes, the electrode 10, which includes the liquid wire 4 for electrical connection between the electrode elements 2, can prevent breakage caused by stress generated by the shape changes. This can reduce changes in resistance associated with expansion and contraction of the liquid wire 4. Reducing the changes in resistance can reduce noise in signals.

When the surface of a living body is measured using the electrode 10, noise caused by shape changes is reduced. Also, when electric stimulation is applied to a living body using the electrode 10, it is possible to reduce changes in electric pulse actually applied in the living body.

Since the plurality of electrode elements 2 are electrically connected by the liquid wire 4, the entire electrode 10 is at the same potential and functions as a single electrode.

Components of the electrode 10 will now be described.

Electrode Elements

Figure 3:
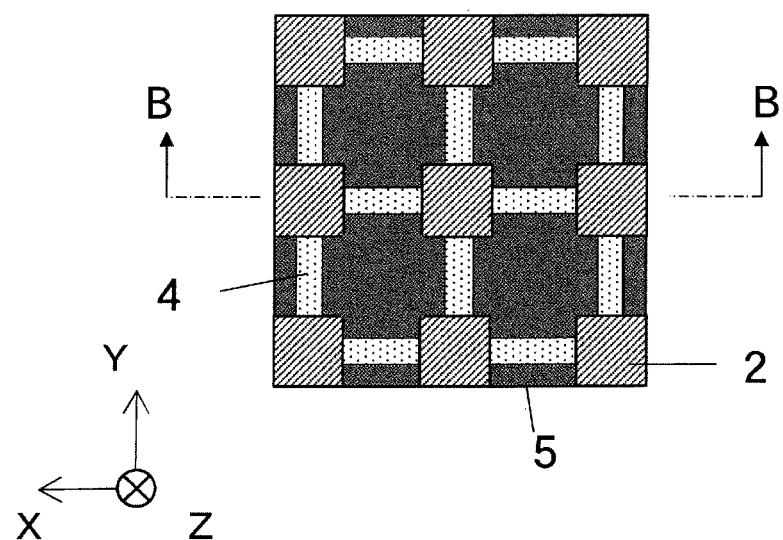
FIG. 3 is a transparent bottom view of a planar arrangement, illustrating in a visible manner a liquid wire of an electrode according to Embodiment 2.
Figure 5:
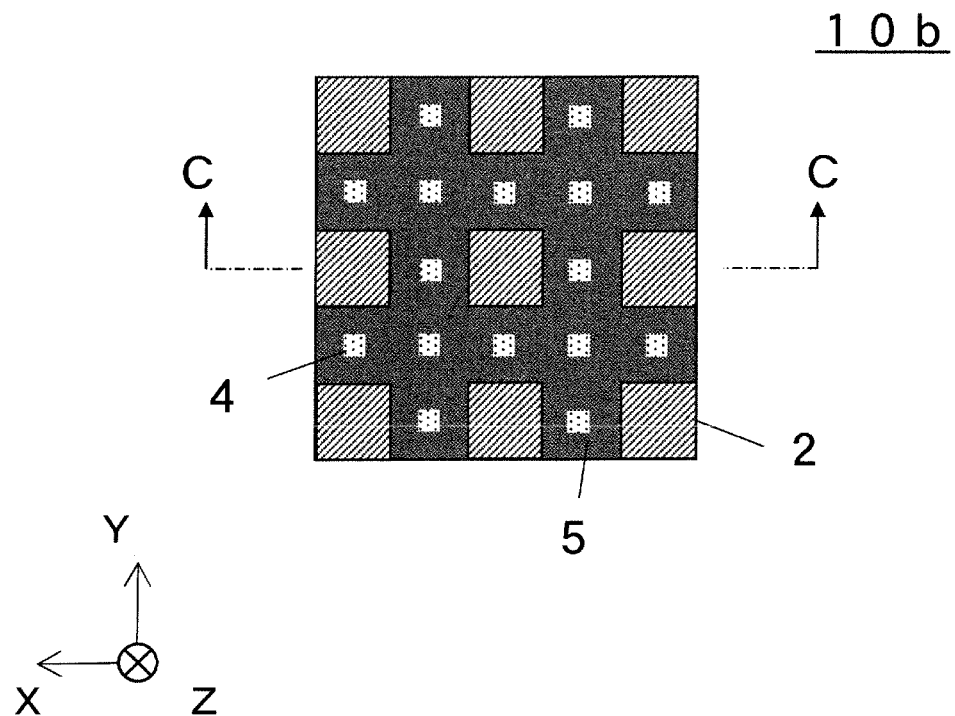
FIG. 5 is a transparent bottom view of a planar arrangement, illustrating in a visible manner a liquid wire of an electrode according to Embodiment 3.

The electrode elements 2 are spaced from each other and disposed to form the first surface 1. The electrode elements 2 are made of a metal, such as copper, silver, gold, or aluminum. The electrode elements 2 may be rectangular in shape, as illustrated in FIG. 1, FIG. 3, and FIG. 5. The shape of the electrode elements 2 is not limited to a rectangle. For example, the electrode elements 2 may be circular, polygonal, or may have a shape containing a straight line and a curve.

Liquid Wire

The liquid wire 4 is a liquid conductor configured to electrically connect the electrode elements 2. The liquid wire 4 is made of, for example, a metal which is liquid at ordinary temperature. For example, the liquid wire 4 is made of a material containing gallium. For example, the liquid wire 4 may be made of a material containing 0% to 40% by weight of indium and 60% to 100% by weight of gallium. The material of the liquid wire 4 is not limited to that described above. The liquid wire 4 may be made of EGaIn (with a melting point of 15.5° C.) containing 75.5% by weight of Ga and 24.5% by weight of In, Galinstan (with a melting point of −19° C.) containing 68.5% by weight of Ga, 21.5% by weight of In, and 10% by weight of Sn, or Galinstan (with a melting point of 10° C.) containing 62% by weight of Ga, 25% by weight of In, and 13% by weight of Sn. These materials, which have melting points lower than human body temperature, can keep the liquid wire 4 in liquid form during use of the electrode, reduce changes in resistance associated with expansion and contraction, and suppress noise.

The configuration of the liquid wire 4 is not limited to the examples described above. For example, as described in Embodiment 6 (FIG. 12), the liquid wire 4 may be a conductive paste containing a liquid resin and a conductive material, such as metal particles, dispersed in the liquid resin.

The liquid wire 4 may be made of a material, such as an alloy having a melting point of lower than or equal to 40° C. That is, as long as the melting point of the alloy is lower than or equal to 40° C., the alloy may have any composition ratio and other metals may be added to the alloy.

The liquid wire may be made of a metal which is liquid at ordinary temperature.

Here, the "ordinary temperature" varies depending on the purpose of use. For example, when the electrode 10 is used as a biomedical electrode, the ordinary temperature is about 15° C. to 25° C., whereas when the electrode 10 is used on a changing surface of a non-living object, the ordinary temperature is about 15° C. to 60° C.

When the length of the liquid wire 4 in one direction parallel to the plane of the liquid wire 4 becomes twice a reference length of the liquid wire 4, the resistance of the liquid wire 4 is less than or equal to 10 times that corresponding to the reference length of the liquid wire. The change in resistance associated with expansion and contraction of the liquid wire 4 can thus be as small as less than or equal to 10 times the resistance corresponding to the reference length. Noise in signals associated with the change in resistance can thus be reduced. The reference length refers to the length of the liquid wire of the electrode not elastically deformed. The resistance of the liquid wire may be directly measured, or may be obtained in other ways. As for the resistance between two electrode elements, the resistance corresponding to a reference distance (i.e., distance between the two electrode elements of the electrode not elastically deformed) is compared to the resistance between the two electrode elements of the electrode elastically deformed in such a way that the distance between the two electrode elements is twice the reference distance. In this case, the change in resistance between the two electrode elements can be as small as less than or equal to 50 times the resistance corresponding to the reference distance.

The liquid wire 4 may extend from one toward the other of two adjacent ones of the electrode elements 2. This can reduce the impact of noise generated when stress is applied in a direction perpendicular to the direction in which the electrode elements 2 extend.

Referring to FIG. 1, in the plane where the electrode elements 2 are arranged, the liquid wire 4 is spaced from and extends between the electrode elements 2 to form a grid pattern.

The perimeter of the liquid wire 4 is sealed. For example, as illustrated in FIG. 1, the liquid wire 4 may be sealed by the solid wire 5, which is a solid conductor. Since this maintains electrical connection between the liquid wire 4 and the solid wire 5, the liquid wire 4 may be electrically connected to the electrode elements 2, with the solid wire 5 therebetween.

The liquid wire 4 may be sealed by a solid insulator. In this case, for example, the liquid wire 4 may be electrically connected to the electrode elements 2 with a conductive via therebetween.

When the substrate 11 supports the electrode elements 2 and the liquid wire 4, the substrate 11 may partially seal the liquid wire 4.

Solid Wire

The solid wire 5 may be made of metal foil, such as copper foil or aluminum foil. The solid wire may be any solid conductor, and is not limited to those described above.

Substrate

The substrate 11 is a planar member disposed on the electrode elements 2 and forming a second surface 3 opposite the first surface 1. The substrate 11 is configured to support the plurality of electrode elements 2 and the liquid wire 4. The substrate 11 may be configured to secure the electrode elements 2 and the liquid wire 4.

The substrate 11 may be a planar member made of a thermoplastic resin, such as urethane resin, acrylic resin, or silicon resin.

Embodiment 2

Figure 4:
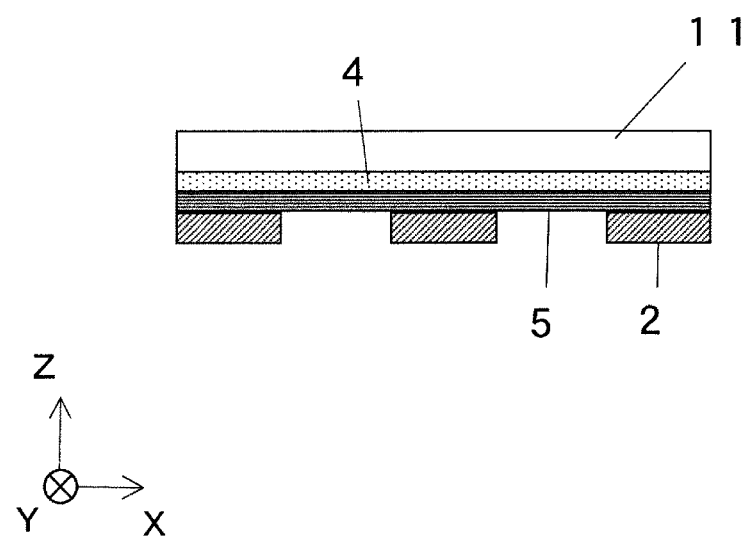
FIG. 4 is a schematic cross-sectional view of a cross-sectional structure viewed in direction B-B of FIG. 3.

FIG. 3 is a transparent bottom view of a planar arrangement, illustrating in a visible manner the liquid wire 4 of an electrode 10a according to Embodiment 2. FIG. 4 is a schematic cross-sectional view of a cross-sectional structure viewed in direction B-B of FIG. 3.

The electrode 10a according to Embodiment 2 differs from the electrode according to Embodiment 1 in that an electrical connection with each of the electrode elements 2 is made in the lamination direction. Specifically, the liquid wire 4 is electrically connected in the lamination direction to each of the electrode elements 2, with the solid wire 5 therebetween.

As illustrated in FIG. 3, in the plane where the electrode elements 2 are arranged, the liquid wire 4 is disposed in a grid pattern to overlap a grid formed by the electrode elements 2, as viewed in the lamination direction. In this case, the grid points of the grid formed by the electrode elements 2 substantially coincide with the respective grid points of the grid of the liquid wire 4.

Embodiment 3

Figure 6:
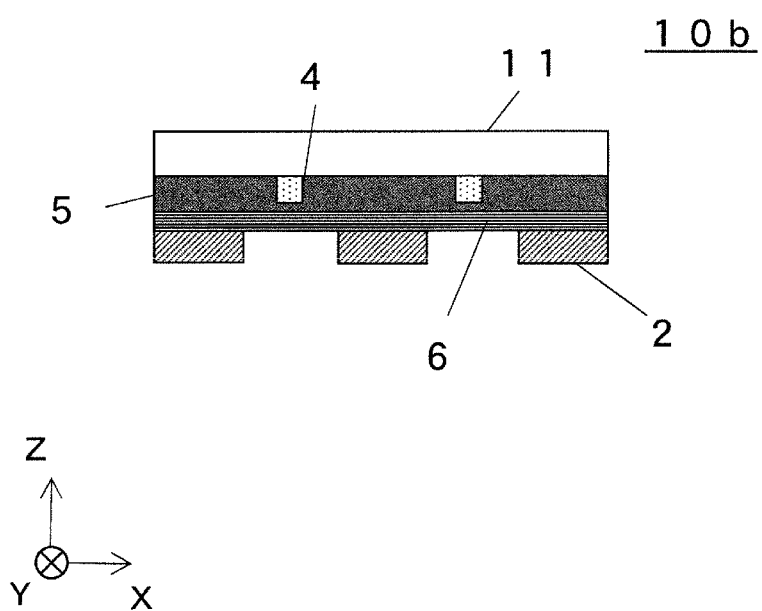
FIG. 6 is a schematic cross-sectional view of a cross-sectional structure viewed in direction C-C of FIG. 5.

FIG. 5 is a transparent bottom view of a planar arrangement, illustrating in a visible manner the liquid wire 4 of an electrode 10b according to Embodiment 3. FIG. 6 is a schematic cross-sectional view of a cross-sectional structure viewed in direction C-C of FIG. 5.

The electrode 10b according to Embodiment 3 differs from the electrodes according to Embodiment 1 and Embodiment 2 in that the liquid wire 4 is in the form of a dotted line, instead of a continuous line. Specifically, as illustrated in FIG. 5, in the plane where the electrode elements 2 are arranged, dots of the liquid wire 4 are spaced from, and distributed between, the electrode elements 2 and located at grid points of the grid.

The liquid wire 4 in the form of a dotted line can also relieve stress caused by shape changes, suppress changes in resistance, and reduce the occurrence of noise.

The electrode 10b according to Embodiment 3 also differs from the electrodes according to Embodiment 1 and Embodiment 2 in that the electrode 10b includes an insulator 6 extending in a planar form between the solid wire 5 and the electrode elements 2. In this case, the liquid wire 4 may be electrically connected to the electrode elements 2, with a via (not shown) made of a conductive material therebetween.
Insulator The insulator 6 extends in a planar form between the solid wire 5 and the electrode elements 2. The insulator 6 may be stretchable. Even when the measured surface of the object to be measured changes and the distance between two adjacent ones of the electrode elements 2 changes, the insulator 6, which is stretchable, can respond to movement of the electrode elements 2 and suppress the occurrence of noise, without suppressing deformation of the liquid wire 4 and elastic deformation the solid wire 5.

The insulator 6 can be made of thermoplastic resin or thermosetting resin.

Embodiment 4

Figure 7:
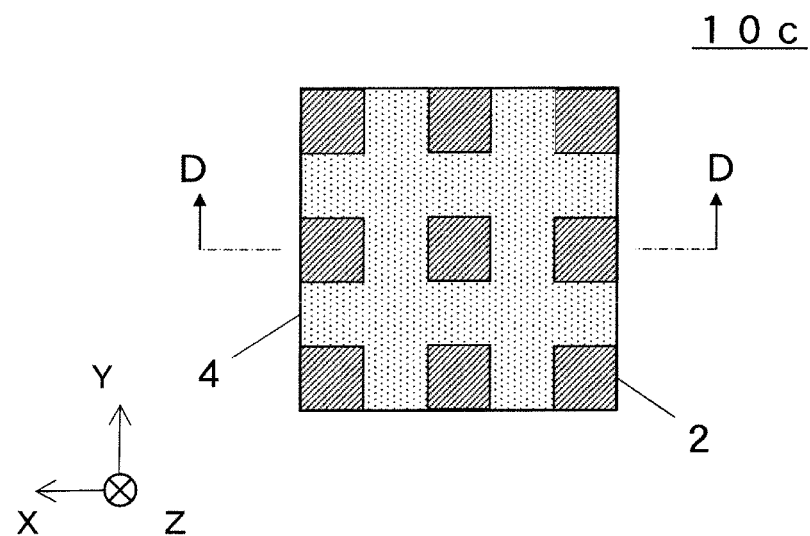
FIG. 7 is a transparent bottom view of a planar arrangement, illustrating in a visible manner a liquid wire of an electrode according to Embodiment 4.
Figure 8:
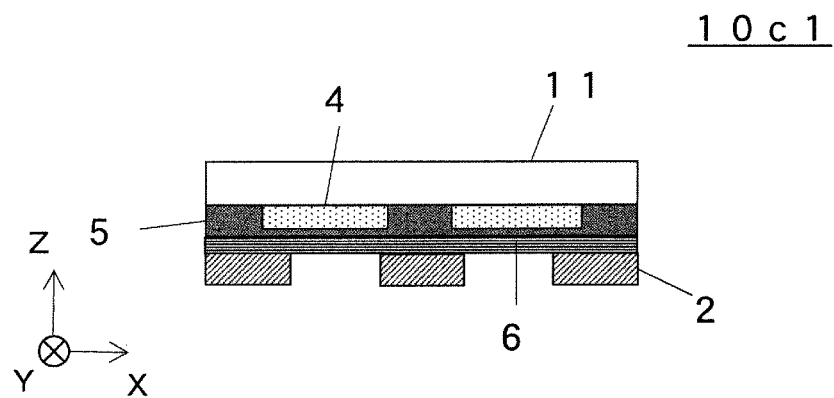
FIG. 8 is a schematic cross-sectional view of an example of a cross-sectional structure viewed in direction D-D of FIG. 7.
Figure 9:
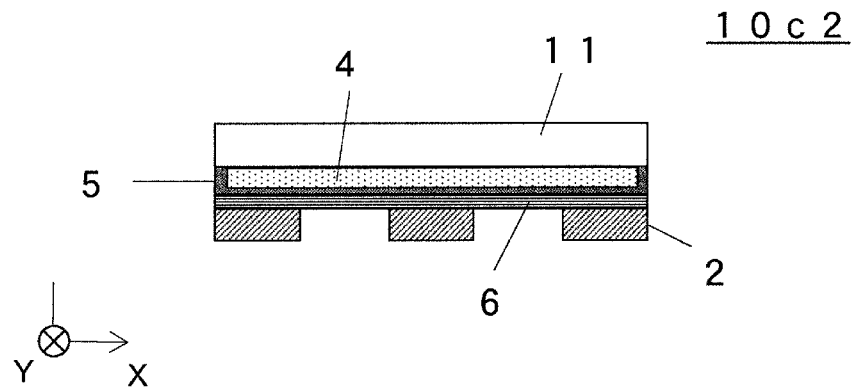
FIG. 9 is a schematic cross-sectional view of another example of the cross-sectional structure viewed in direction D-D of FIG. 7.

FIG. 7 is a transparent bottom view of a planar arrangement, illustrating in a visible manner the liquid wire 4 of an electrode 10c according to Embodiment 4. FIG. 8 is a schematic cross-sectional view of an example of a cross-sectional structure viewed in direction D-D of FIG. 7. FIG. 9 is a schematic cross-sectional view of another example of the cross-sectional structure viewed in direction D-D of FIG. 7.

As illustrated in FIG. 7, the electrode 10c according to Embodiment 4 differs from the electrodes according to Embodiments 1 to 3 in that the liquid wire 4 extends across the gaps between adjacent ones of the electrode elements 2 in plan view. Examples of the arrangement of the liquid wire 4 are illustrated in FIG. 8 and FIG. 9. In FIG. 8 illustrating a cross section of an electrode 10c1, the liquid wire 4 extends beyond the width of each gap between adjacent ones of the electrode elements 2. Alternatively, as in FIG. 9 illustrating a cross section of an electrode 10c2, the liquid wire 4 may extend over the entire back side of the electrode elements 2.

Embodiment 5

Figure 10:
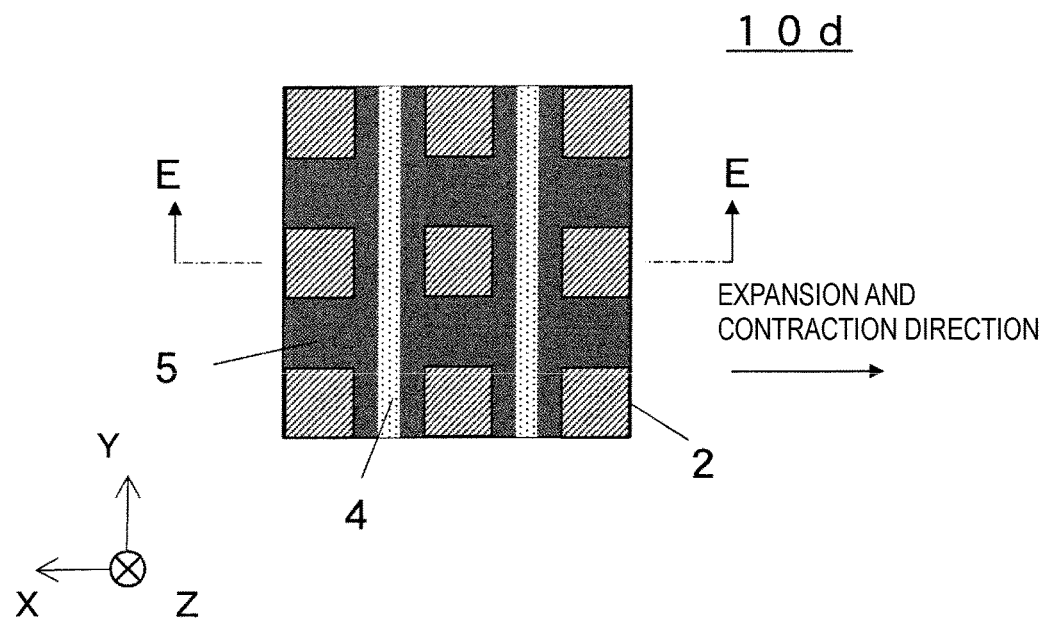
FIG. 10 is a transparent bottom view of a planar arrangement, illustrating in a visible manner a liquid wire of an electrode according to Embodiment 5.
Figure 11:
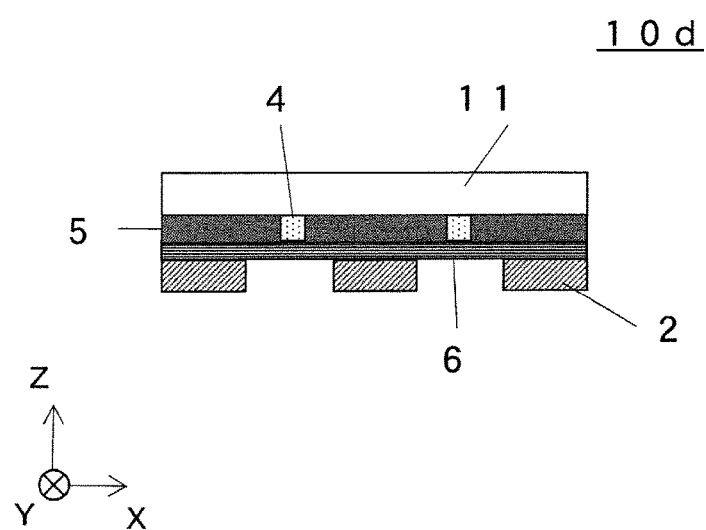
FIG. 11 is a schematic cross-sectional view of an example of a cross-sectional structure viewed in direction E-E of FIG. 10.

FIG. 10 is a transparent bottom view of a planar arrangement, illustrating in a visible manner the liquid wire 4 of an electrode 10d according to Embodiment 5. FIG. 11 is a schematic cross-sectional view of an example of a cross-sectional structure viewed in direction E-E of FIG. 10.

The electrode 10d according to Embodiment 5 differs from the electrodes according to Embodiments 1 to 4 in that the liquid wire 4 extends in one direction.

Referring to FIG. 10, the liquid wire 4 extends in a direction perpendicular to an expansion and contraction direction. This allows the liquid wire 4 to deform in response to expansion and contraction, and can reduce changes in resistance and suppress the occurrence of noise. The expansion and contraction direction refers to the direction in which less force is required to elastically deform the electrode. For example, when the same tension is applied to elastically deform the electrode, the length by which the electrode is elastically deformed and stretched by applying tension in the expansion and contraction direction is longer than the length by which the electrode is elastically deformed and stretched by applying tension in a direction different from the expansion and contraction direction.

Embodiment 6

FIG. 12A is a schematic cross-sectional view illustrating a cross-sectional structure of an electrode 10e according to Embodiment 6, and FIG. 12B is an enlarged cross-sectional view illustrating a detailed cross-sectional structure of a liquid wire 4a illustrated in FIG. 12A.

The electrode 10e according to Embodiment 6 is characterized in that the liquid wire 4a contains a matrix of liquid resin 12 and a conductive material 14 dispersed in the matrix. The liquid wire 4a may be, for example, a silver paste in liquid form used as it is without being baked or dried. The liquid wire 4a is not limited to a silver paste, and may be any conductive paste containing the liquid resin 12 and the conductive material 14 dispersed in the liquid resin 12.

Although the liquid wire 4a is not entirely made of a conductive material in this case, it is still possible to allow the liquid wire 4a to deform in response to expansion and contraction, reduce changes in resistance, and suppress the occurrence of noise.

The conductive material 14 may be liquid or solid, but is not limited to this. The liquid wire 4a may be, for example, a conductive aqueous solution containing a matrix of aqueous solution and an electrolyte dissolved in the matrix.

Embodiment 7

FIG. 13 is a schematic cross-sectional view illustrating a cross-sectional structure of an electrode 10f according to Embodiment 7.

The electrode 10f according to Embodiment 7 differs from the electrode according to Embodiment 1 in that the electrode 10f includes the insulator 6. With the insulator 6 between adjacent ones of the electrode elements 2, it is possible, outside the electrode elements 2, to reduce contact with the object to be measured.

Embodiment 8

Figure 14:
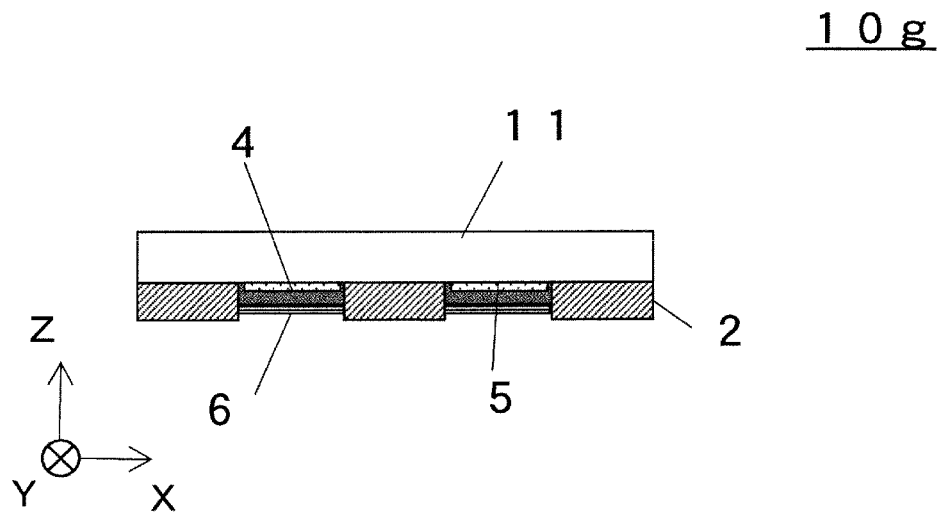
FIG. 14 is a schematic cross-sectional view illustrating a cross-sectional structure of an electrode according to Embodiment 8.

FIG. 14 is a schematic cross-sectional view illustrating a cross-sectional structure of an electrode 10g according to Embodiment 8.

The electrode 10g according to Embodiment 8 differs from the electrode according to Embodiment 7 in that the liquid wire 4 extends across the gaps between adjacent ones of the electrode elements 2. This allows the liquid wire 4 to directly receive expansion and contraction between the electrode elements 2.

Figure 15A:
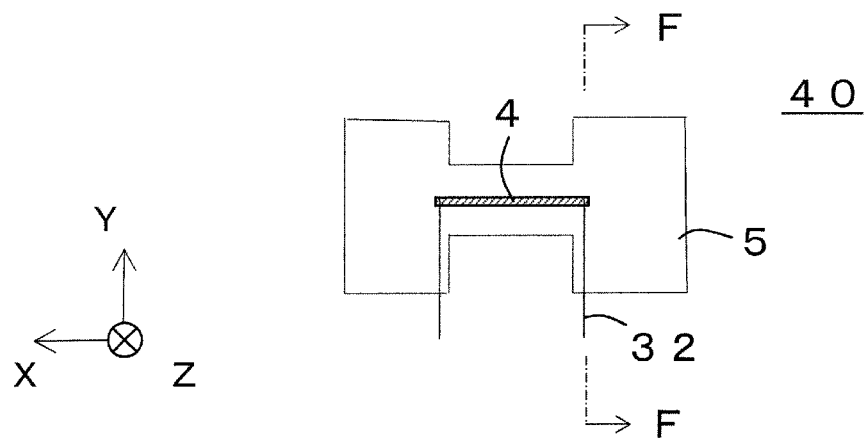
FIG. 15A is a plan view of an electrode including a liquid wire for a test.
Figure 15B:
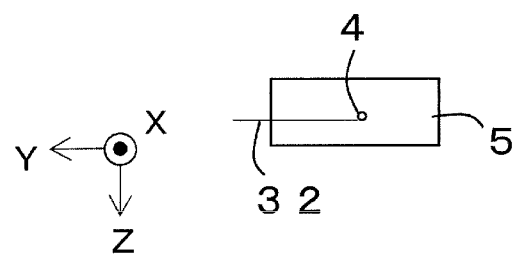
FIG. 15B is a schematic cross-sectional view illustrating a cross-sectional structure of the electrode viewed in direction F-F of FIG. 15A.
Figure 16A:
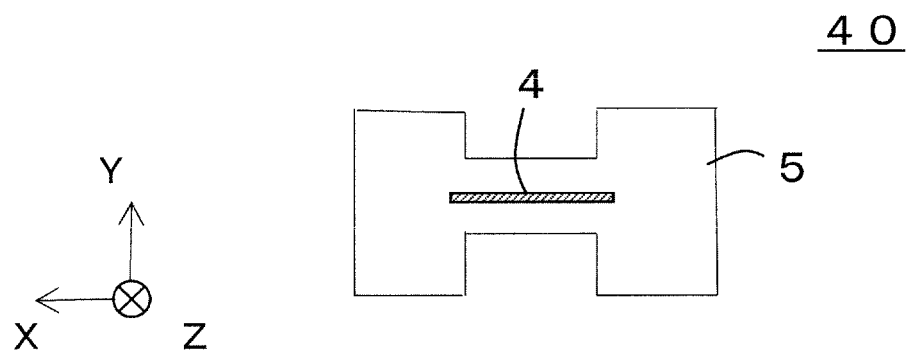
FIG. 16A is a plan view of the same electrode as that in FIG. 15A.
Figure 16B:
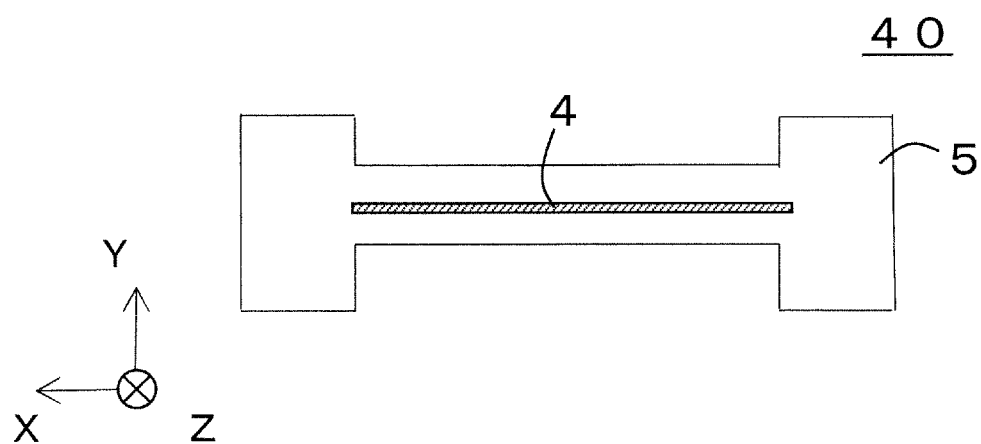
FIG. 16B is a plan view illustrating the electrode of FIG. 16A deformed by tensile force applied thereto in an X direction.

The wiring pattern of the liquid wire is not limited to the examples described above, and various wiring patterns can be selected within the range of the present disclosure. For example, the wiring pattern may be a grid, linear, dotted, or planar pattern. The solid wire and the insulator are replaceable as long as electrical connection between the liquid wire and the electrode elements can be maintained.
Noise Generated in Liquid Wire FIG. 15A is a plan view of an electrode 40 including the liquid wire 4 for a test, and FIG. 15B is a schematic cross-sectional view illustrating a cross-sectional structure of the electrode 40 viewed in direction F-F of FIG. 15A. FIG. 16A is a plan view of the same electrode 40 as that in FIG. 15A, and FIG. 16B is a plan view illustrating the electrode 40 of FIG. 16A deformed by tensile force applied thereto in the X direction.

With reference to FIG. 15A to FIG. 16B, noise generated in the sealed liquid wire 4 under tensile force will be described. As illustrated in FIG. 15A, the electrode 40 having an H-shape is prepared. The electrode 40 includes, for example, the liquid wire 4 sealed with the solid wire 5 containing silicon resin, and a pair of conductors 32 connected to the liquid wire 4. The impedance of the liquid wire 4 can be measured by taking out the pair of conductors connected to the liquid wire 4. The conductors 32 are disposed at both end portions of the liquid wire 4 in a first direction (X direction) in which the liquid wire 4 extends. After an impedance $R_0$ in the initial state is measured, a tensile force is applied to the electrode 40 in the first direction (X direction) in such a way that an expansion ratio of 100% is reached. Then, an impedance R is measured at an expansion ratio of 100%. An expansion ratio of 100% means that the liquid wire 4 is 2× in length, where X is the length from one end to the other end of the liquid wire 4 in the first direction (X direction) under no tensile force. On the other hand, an expansion ratio of 0% means that the liquid wire 4 is X in length from one end to the other end thereof in the first direction (X direction).

Table 1 compares resistance change ratios at an expansion ratio of 100% between electrodes, one including a liquid wire made of a conductive paste (e.g., Ag paste) and the other including a liquid wire made of a liquid metal. Assume that the impedance $R_0$ at an expansion ratio of 0% (length X) is 1Ω in both the electrodes. When subjected to a tensile force until an expansion ratio of 100% (length 2×) was achieved, the electrode including the liquid wire made of a conductive paste had the impedance R (resistance: 130Ω) 130 times the impedance $R_0$, whereas the electrode including the liquid wire made of a liquid metal had the impedance R (resistance: 3Ω) about 3 times the impedance $R_0$. This indicates that the liquid wire made of a liquid metal generates less noise than the liquid wire made of a conductive paste.

The liquid wire 4 may be made of an electrolyte aqueous solution. The liquid wire 4 may be made of an aqueous solution containing metal powder, or may be made of an aqueous solution containing metal coated with conductive resin.

TABLE 1

| Liquid wire | Resistance change ratio at expansion ratio of 100%: $(R - R_0)/R_0 \times 100$ [%] |
|---|---|
| Conductive paste | 130 |
| Liquid metal | 3 |

In Table 1, $R_0$ is the impedance (resistance) of the liquid wire before being stretched (expansion ratio of 0%), and R is the impedance (resistance) of the liquid wire being stretched (expansion ratio of 100%).

The definition of the expansion ratio is not limited to this. For example, when there are two adjacent electrode elements, with a liquid wire therebetween, an expansion ratio of 100% may mean that the distance between the two electrode elements is 2×, where X is the distance from one end to the other end of each electrode element under no external pressure.

Embodiment 9

Figure 17A:
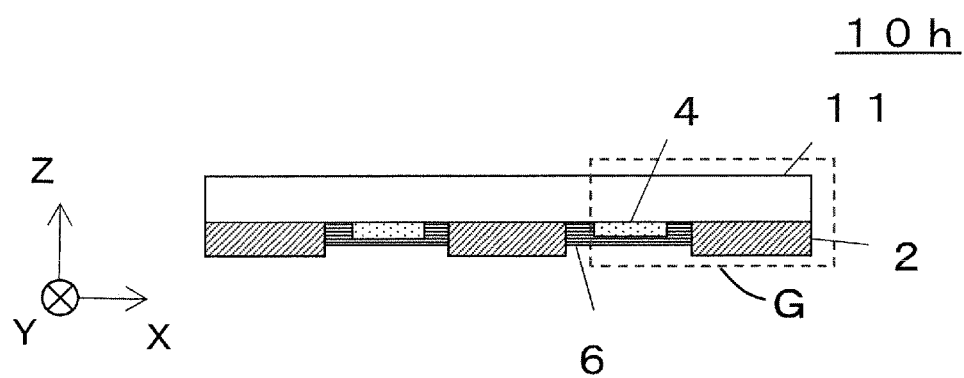
FIG. 17A is a schematic cross-sectional view illustrating a cross-sectional structure of an electrode according to Embodiment 9.
Figure 17B:
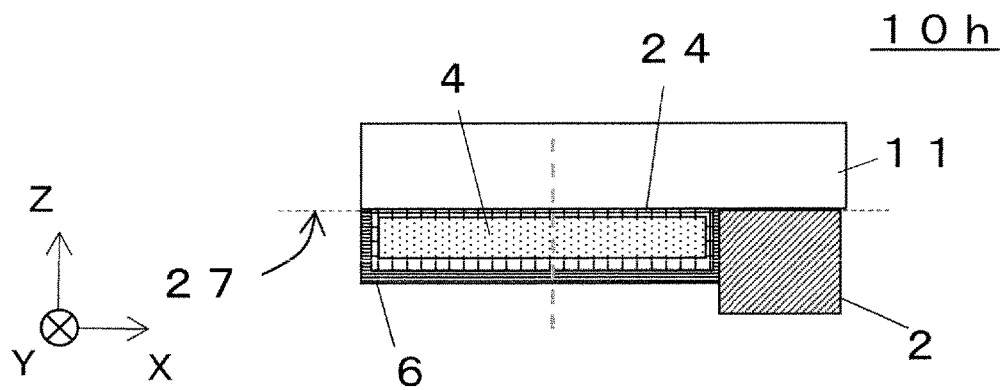
FIG. 17B is an enlarged cross-sectional view of dotted region G in FIG. 17A, including one electrode element at an end portion of the electrode.
Figure 17C:
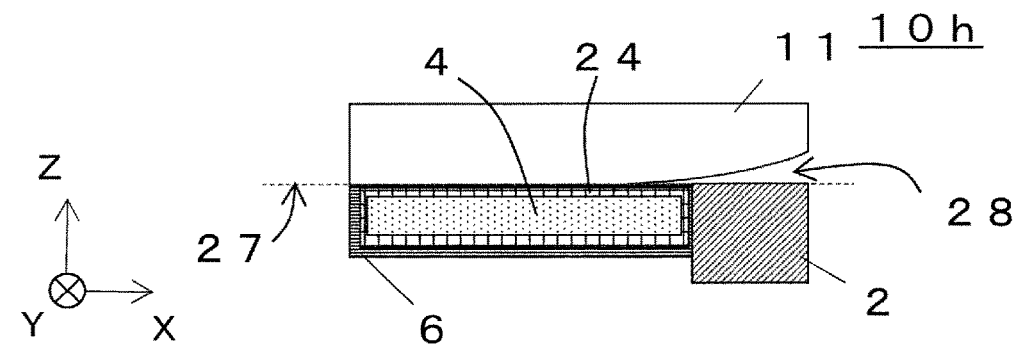
FIG. 17C is an enlarged cross-sectional view illustrating a separation at the end portion of the electrode illustrated in FIG. 17B.
Figure 17D:
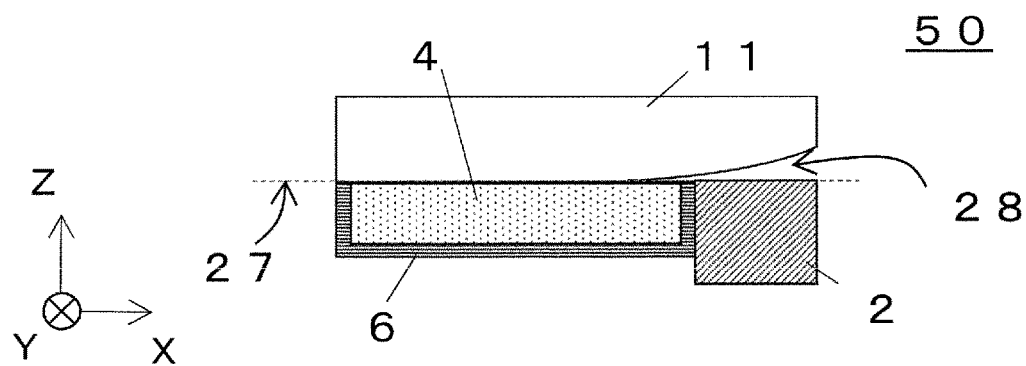
FIG. 17D is an enlarged cross-sectional view illustrating a separation in an electrode of a reference example which does not include a sealing portion for sealing the liquid wire.

FIG. 17A is a schematic cross-sectional view illustrating a cross-sectional structure of an electrode 10h according to Embodiment 9. FIG. 17B is an enlarged cross-sectional view of dotted region G in FIG. 17A, including one electrode element at an end portion of the electrode 10h. FIG. 17C is an enlarged cross-sectional view illustrating a separation 28 at the end portion of the electrode 10h illustrated in FIG. 17B. FIG. 17D is an enlarged cross-sectional view illustrating the separation 28 in an electrode 50 of a reference example which does not include a sealing portion for sealing the liquid wire.

As illustrated in FIG. 17B, the electrode 10h according to Embodiment 9 differs from the electrode according to Embodiment 1 in that the electrode 10h includes a sealing portion 24 for sealing the liquid wire 4. The sealing portion 24 may have conductivity which allows conduction between the liquid wire 4 and the electrode elements 2. In the electrode 10h, as illustrated in FIG. 17C, even when the separation 28 occurs at a seam 27 in resin between the substrate 11 and the electrode element 2 and the liquid wire 4, leakage from the liquid wire 4 does not occur because the liquid wire 4 is sealed with the sealing portion 24. In the electrode 50 of the reference example which does not include a sealing portion, as illustrated in FIG. 17D, the separation 28 between the substrate 11 and the electrode element 2 and the wire 4 may cause leakage from the liquid wire 4.

Sealing Portion

The sealing portion 24 is required to simply seal the perimeter of the liquid wire 4. Although the sealing portion 24 illustrated in FIG. 17B seals the entire perimeter of the liquid wire 4, the configuration is not limited to this. The sealing portion 24 may seal the liquid wire 4 on a predetermined unit basis. For example, the entire liquid wire 4 on the surface may be covered with a single integral sealing portion. A plurality of sealing portions may seal the liquid wire on a row-by-row or column-by-column basis. A plurality of sealing portions may seal the liquid wire on a unit area basis. When a plurality of sealing portions seal the liquid wire on a region-by-region basis, it is simply required that conduction be achieved between adjacent ones of the sealing portions.

The sealing portion 24 may be made of a stretchable resin, such as elastomer, PDMS, or PVP, or may be made of hydrogel. The sealing portion 24 may be made of a fibrous material, such as polyurethane, or may be made of tungsten oxide, copper, or gallium oxide ($Ga_2O_3$). The sealing portion 24 is not limited to one that is formed by a single component. For example, the sealing portion 24 may be made of a composite of materials, such as resin and copper. The sealing portion 24 may be an insulating portion, or may have conductivity to allow conduction with the electrode elements. As described below, the sealing portion may include a first sealing portion on the inner side and a second sealing portion on the outer side. In this case, the first sealing portion may be a conductive sealing portion, and the second sealing portion may be an insulating sealing portion. The first sealing portion on the inner side may be a solid wire. The second sealing portion on the outer side may be an insulator. The sealing portion may also be referred to as a supporter or a protective layer, depending on the function.

The sealing portion 24 may contain a porous material. For example, the porous material may be a sponge containing resin. With the sealing portion 24 containing a porous material, the porous material retains liquid forming the liquid wire 4. The porous material, which is solid, makes the liquid wire 4 resistant to deformation and this can reduce noise. The porous material can effectively reduce deformation of the liquid wire 4 particularly when the electrode 10$h$ is deformed. Beside resin, the porous material may contain cloth or metal. The porous material may be, for example, a nonwoven fabric.

Embodiment 10

Figure 18:
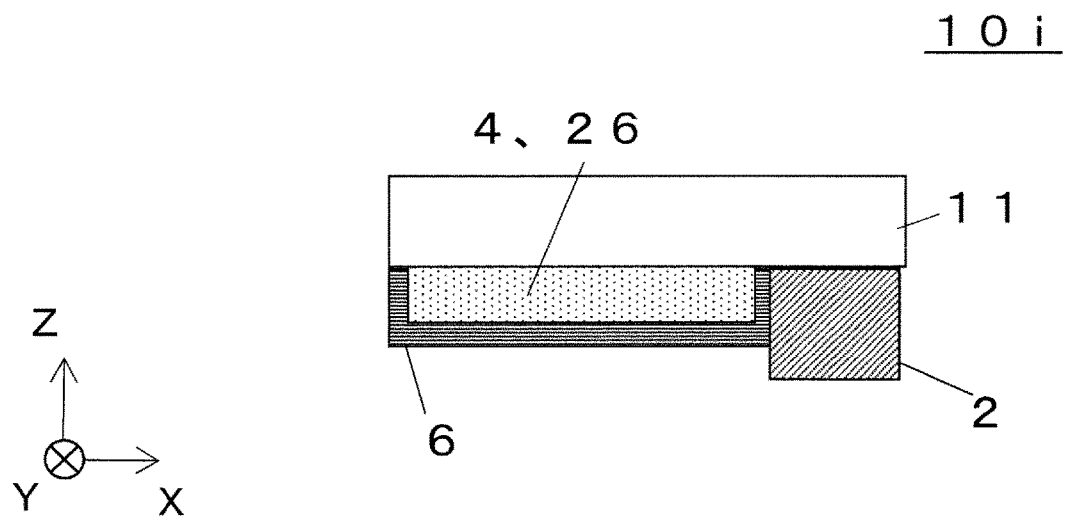
FIG. 18 is a schematic cross-sectional view illustrating a cross-sectional structure of an electrode according to Embodiment 10.

FIG. 18 is a schematic cross-sectional view illustrating a cross-sectional structure of an electrode 10$i$ according to Embodiment 10.

As illustrated in FIG. 18, the electrode 10$i$ according to Embodiment 10 differs from the electrode according to Embodiment 1 in that the liquid wire 4 contains a porous material 26. The porous material 26 is, for example, a sponge containing resin. With the liquid wire 4 containing a porous material, the porous material retains liquid forming the liquid wire 4. The porous material, which is solid, makes the liquid wire 4 resistant to deformation and this can reduce noise. The porous material can effectively reduce deformation of the liquid wire 4 particularly when the electrode 10$i$ is deformed. Beside resin, the porous material 26 may contain cloth or metal. The porous material 26 may be, for example, a nonwoven fabric.

Embodiment 11

Figure 19A:
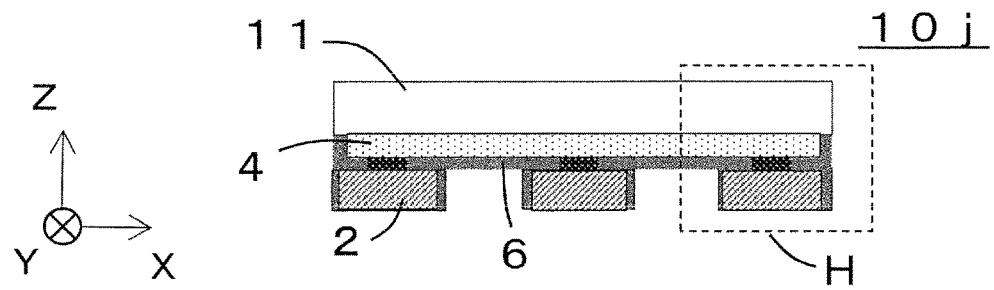
FIG. 19A is a schematic cross-sectional view illustrating a cross-sectional structure of an electrode according to Embodiment 11.
Figure 19B:
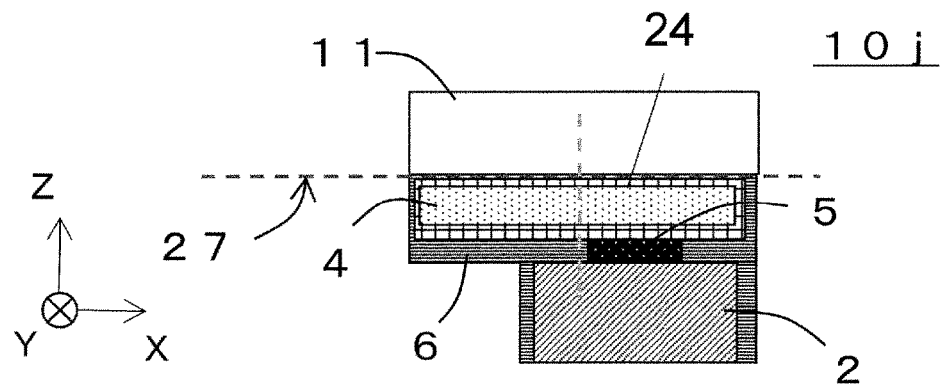
FIG. 19B is an enlarged cross-sectional view of dotted region H in FIG. 19A, including one electrode element at an end portion of the electrode.
Figure 19C:
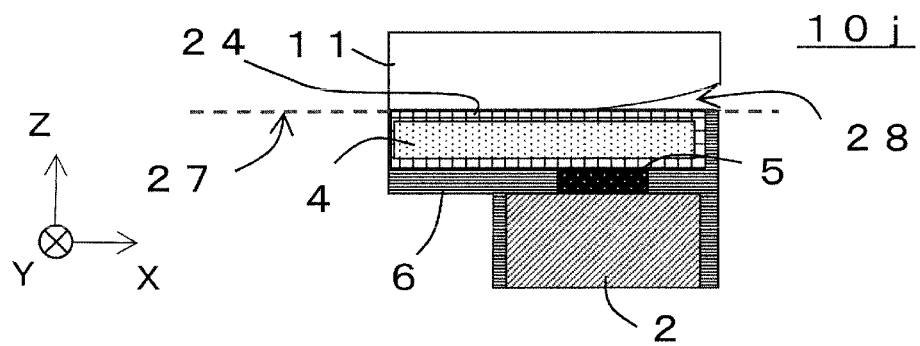
FIG. 19C is an enlarged cross-sectional view illustrating a separation at the end portion of the electrode illustrated in FIG. 19B.
Figure 19D:
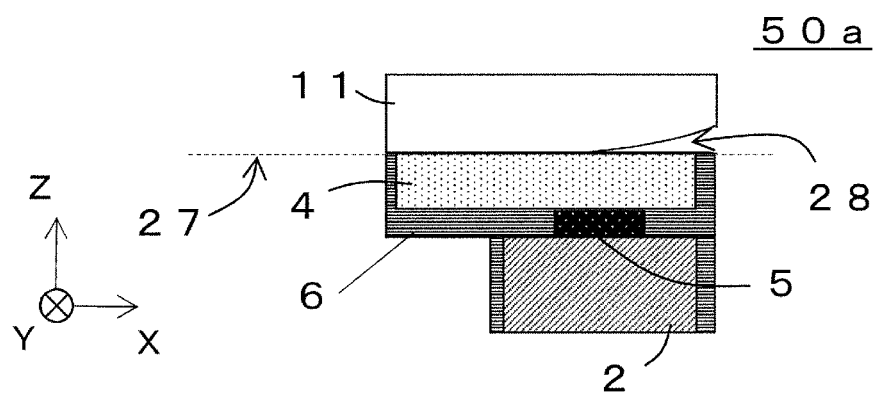
FIG. 19D is an enlarged cross-sectional view illustrating a separation in an electrode of a reference example which does not include a sealing portion for sealing the liquid wire.

FIG. 19A is a schematic cross-sectional view illustrating a cross-sectional structure of an electrode 10$j$ according to Embodiment 11. FIG. 19B is an enlarged cross-sectional view of dotted region H in FIG. 19A, including one electrode element 2 at an end portion of the electrode 10$j$. FIG. 19C is an enlarged cross-sectional view illustrating the separation 28 at the end portion of the electrode 10$j$ illustrated in FIG. 19B. FIG. 19D is an enlarged cross-sectional view illustrating the separation 28 in an electrode 50$a$ of a reference example which does not include a sealing portion for sealing the liquid wire 4.

As illustrated in FIG. 19B, the electrode 10$j$ according to Embodiment 11 differs from the electrode according to Embodiment 1 in that the electrode 10$j$ includes the sealing portion 24 for sealing the liquid wire 4. In the electrode 10$j$, as illustrated in FIG. 19C, even when the separation 28 occurs at the seam 27 in resin between the substrate 11 and the electrode element 2 and the liquid wire 4, leakage from the liquid wire 4 does not occur, because the liquid wire 4 is sealed with the sealing portion 24. In the electrode 50$a$ of the reference example which does not include a sealing portion, as illustrated in FIG. 19D, the separation 28 between the substrate 11 and the electrode element 2 and the liquid wire 4 may cause leakage from the liquid wire 4.

Embodiment 12

Figure 20A:
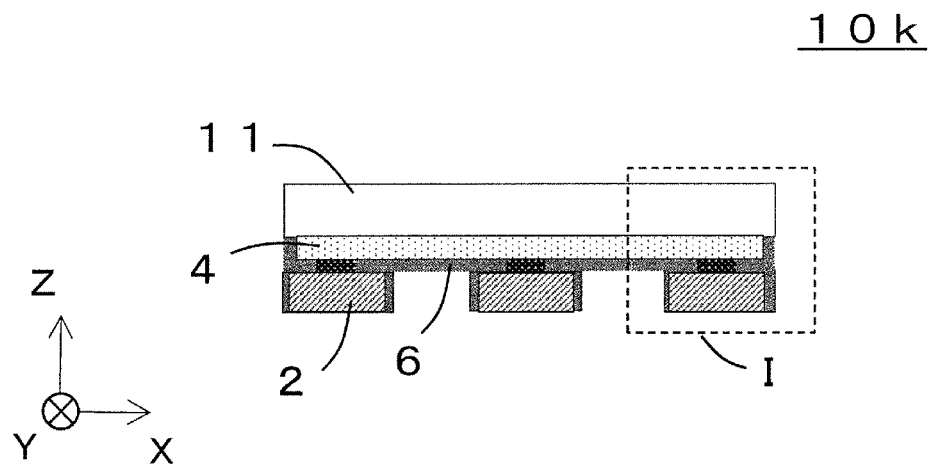
FIG. 20A is a schematic cross-sectional view illustrating a cross-sectional structure of an electrode according to Embodiment 12.
Figure 20B:
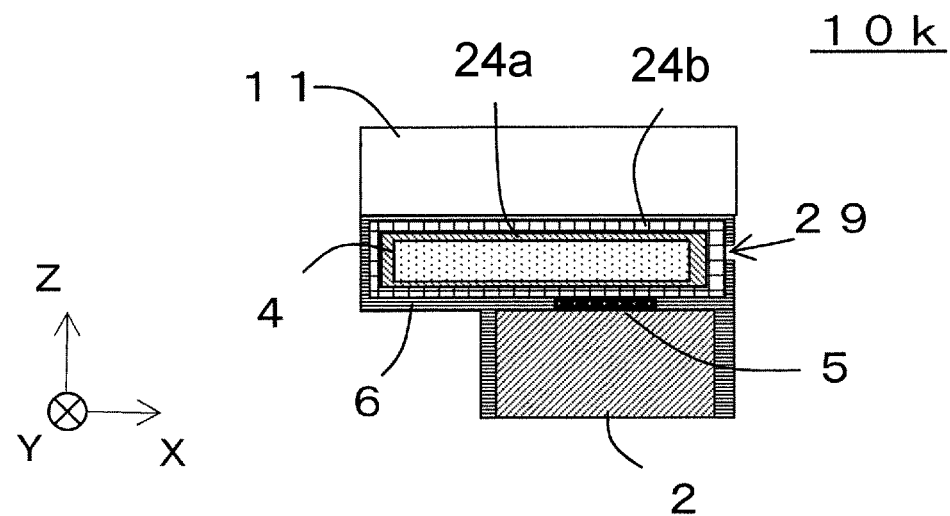
FIG. 20B is an enlarged cross-sectional view of dotted region I in FIG. 20A, including one electrode element at an end portion of the electrode, the enlarged cross-sectional view illustrating a crack at the end portion of the electrode.
Figure 20C:
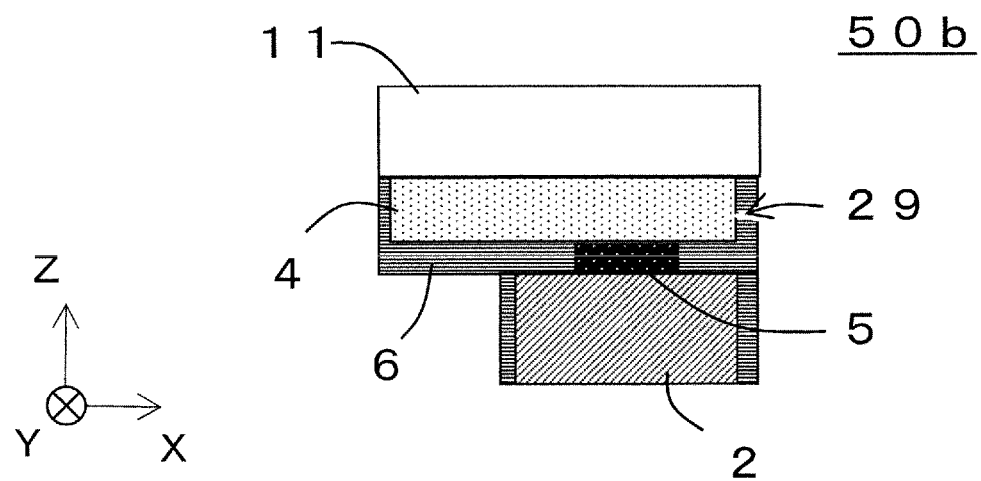
FIG. 20C is an enlarged cross-sectional view illustrating a crack in an electrode of a reference example which does not include a sealing portion for sealing the liquid wire.

FIG. 20A is a schematic cross-sectional view illustrating a cross-sectional structure of an electrode 10$k$ according to Embodiment 12. FIG. 20B is an enlarged cross-sectional view of dotted region I in FIG. 20A, including one electrode element 2 at an end portion of the electrode 10$k$. FIG. 20B illustrates a crack 29 at the end portion of the electrode 10$k$. FIG. 20C is an enlarged cross-sectional view illustrating a crack in an electrode of a reference example which does not include a sealing portion for sealing the liquid wire.

As illustrated in FIG. 20B, the electrode 10$k$ according to Embodiment 12 differs from the electrode according to Embodiment 1 in that the electrode 10$k$ includes a first sealing portion 24$a$ for sealing the liquid wire 4 and a second sealing portion 24$b$ disposed outside the first sealing portion 24$a$. The first sealing portion 24$a$ and the second sealing portion 24$b$ function as a solid wire. In the electrode 10$k$, even if the insulator 6 is broken by sudden expansion and contraction or external force, the first sealing portion 24$a$ and the second sealing portion 24$b$ can reduce leakage of liquid from the liquid wire4.

The first sealing portion 24$a$ is disposed on the inner side of the electrode 10$k$, and the second sealing portion 24$b$ is disposed outside the first sealing portion24$a$. The first sealing portion 24$a$ and the second sealing portion 24$b$ may have different moduli of elasticity. For example, if the relation "modulus of elasticity of the first sealing portion 24$a$>modulus of elasticity of the second sealing portion 24$b$" holds true, then even if the electrode 10$k$ is subjected to pressure, the resulting noise can be reduced. This is because the second sealing portion 24$a$ deforms to absorb the pressure, and the first sealing portion 24$a$ is more resistant to deformation than the second sealing portion 24$b$.

On the other hand, if the relation "modulus of elasticity of the first sealing portion 24$a$<modulus of elasticity of the second sealing portion 24$b$" holds true, then even if the second sealing portion 24$b$ is damaged by pressure applied to the electrode 10$k$, the damage to the second sealing portion 24$b$ does not significantly affect the first sealing portion 24$a$, which is more deformable. With the first sealing portion 24$a$ resistant to damage, the leakage of liquid forming the liquid wire to the outside is reduced. This can prevent the occurrence of noise caused by leakage to the outside.

The first sealing portion 24$a$ and the second sealing portion 24$b$ may be separate and movable with respect to each other. In this case, even if the second sealing portion 24$b$ is damaged by pressure applied to the electrode 10$k$, the damage to the second sealing portion 16$b$ does not significantly affect the first sealing portion 24$a$, because the first sealing portion 24$a$ and the second sealing portion 24$b$ are movable with respect to each other.

The first sealing portion 24$a$ and the second sealing portion 24$b$ may have different colors. The different colors allow the user to identify any damage to the second sealing portion 24$b$. This can prevent the liquid forming the liquid wire from leaking to the outside.

Embodiment 13

Figure 21A:
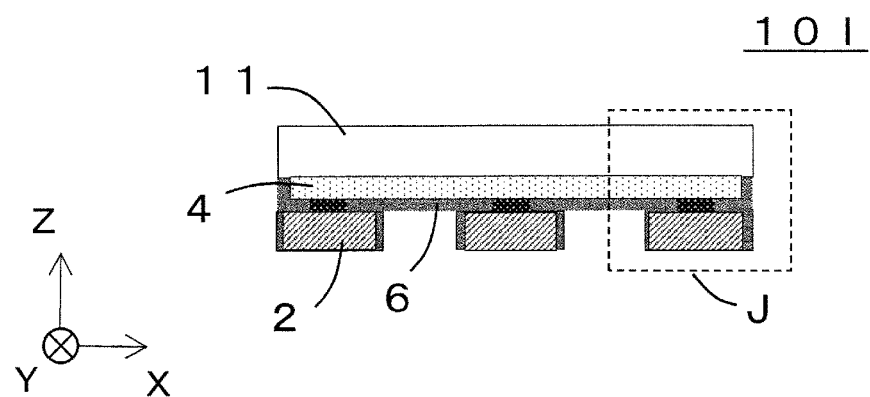
FIG. 21A is a schematic cross-sectional view illustrating a cross-sectional structure of an electrode according to Embodiment 13.
Figure 21B:
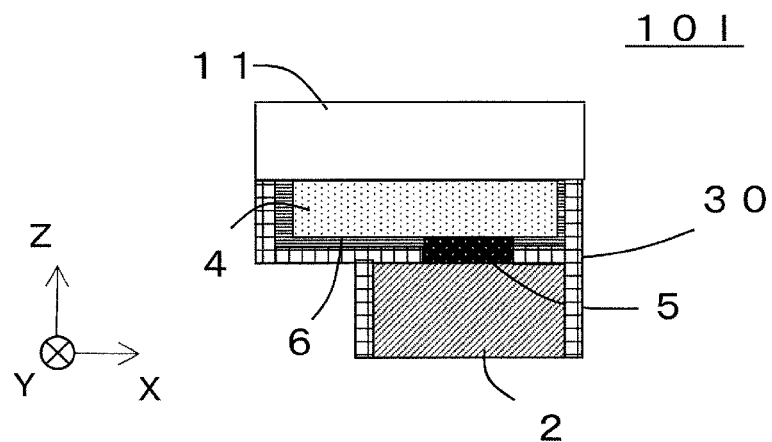
FIG. 21B is an enlarged cross-sectional view of dotted region J in FIG. 21A, including one electrode element at an end portion of the electrode.
Figure 21C:
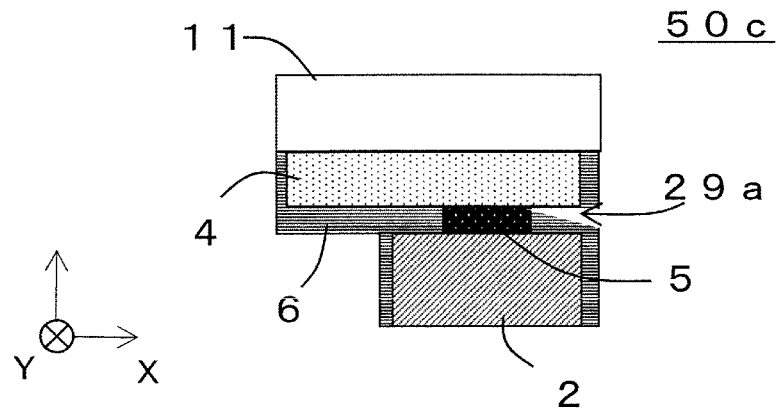
FIG. 21C is an enlarged cross-sectional view illustrating a crack in an electrode of a reference example which does not include a sealing portion serving as a protective layer covering an outer side portion of an insulator.

FIG. 21A is a schematic cross-sectional view illustrating a cross-sectional structure of an electrode 101 according to Embodiment 13. FIG. 21B is an enlarged cross-sectional view of dotted region J in FIG. 21A, including one electrode element 2 at an end portion of the electrode 101. FIG. 21C is an enlarged cross-sectional view illustrating a crack 29$a$ in an electrode 50$c$ of a reference example which does not include a sealing portion serving as a protective layer covering an outer side portion of the insulator.

As illustrated in FIG. 21B, the electrode 101 according to Embodiment 13 differs from the electrode according to Embodiment 1 in that the electrode 101 includes a sealing portion 30 serving as a protective layer covering the outer side portion of the insulator 6. In the electrode 101, even if the insulator 6 is broken by sudden expansion and contraction or external force, the sealing portion 30 serving as a protective layer covering the outer side portion of the insulator 6 can reduce leakage of liquid from the liquid wire.

Embodiment 14

Figure 22A:
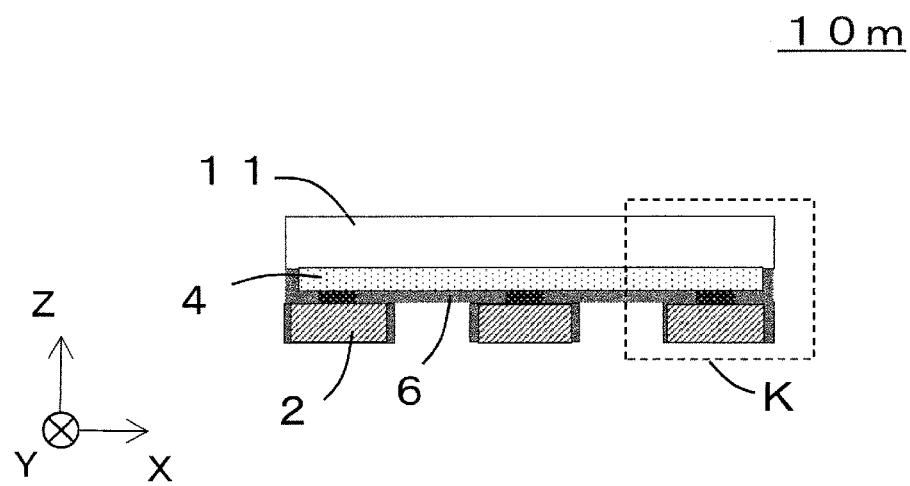
FIG. 22A is a schematic cross-sectional view illustrating a cross-sectional structure of an electrode according to Embodiment 14.
Figure 22B:
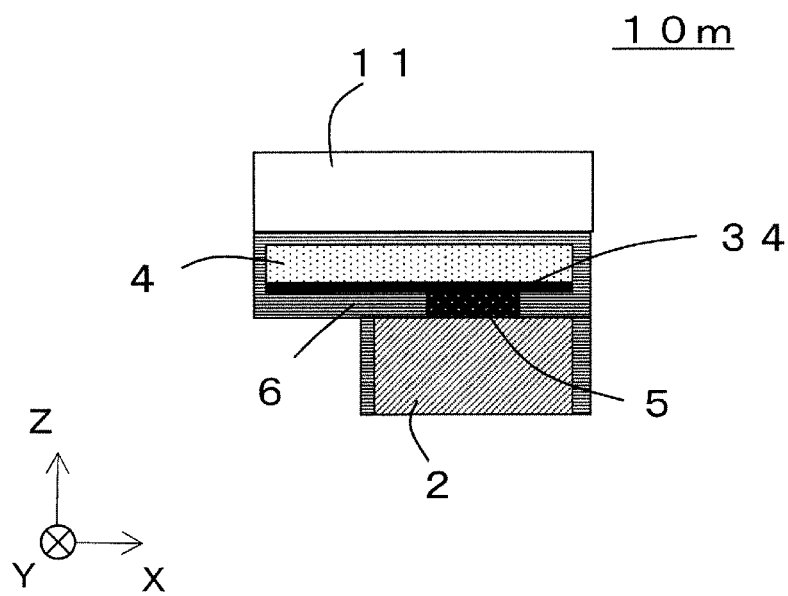
FIG. 22B is an enlarged cross-sectional view of dotted region K in FIG. 22A, including one electrode element at an end portion of the electrode.

FIG. 22A is a schematic cross-sectional view illustrating a cross-sectional structure of an electrode 10*m* according to Embodiment 14. FIG. 22B is an enlarged cross-sectional view of dotted region K in FIG. 22A, including one electrode element 2 at an end portion of the electrode 10*m*.

As illustrated in FIG. 22B, the electrode 10*m* according to Embodiment 14 differs from the electrode according to Embodiment 1 in that the electrode 10*m* includes a magnet 34 near the electrode element 2. In this case, the liquid wire may contain a ferromagnetic material, such as Fe, Ni, or Co. The magnet 34 allows the liquid wire 4 containing a ferromagnetic material to be held near wiring of the electrode 10*m*. This can suppress the occurrence of noise even when the shape of the electrode 10*m* changes. In plan view of the magnet 34 viewed in a direction normal to the upper surface of the substrate 11, the magnet 34 preferably overlaps the electrode element 2.

Higher wettability between the liquid wire and the electrode elements can provide better conductivity. The wettability of the electrode elements can be improved, for example, by making the surface roughness of the electrode elements as small as 1 μm or less. With a conductive liquid layer (referred to as "slip layer"), such as an electrolyte layer, between the liquid wire and the electrode elements, the wettability between the liquid wire and the electrode elements can be improved. For improved wettability, for example, the degree of humidity between the liquid wire and the electrode elements is preferably a relative humidity of greater than or equal to 50%, and more preferably greater than or equal to 75%.

According to Aspect 11, in the electrode of Aspect 2, the liquid wire may contain a ferromagnetic material, the electrode may further include a magnet configured to attract the ferromagnetic material, and in plan view of the magnet viewed in a direction normal to the first surface, the magnet may overlap at least one of the electrode elements.

According to Aspect 12, in the electrode of any one of Aspects 1 to 11, the electrode may further include a sealing portion configured to seal the liquid wire, and the sealing portion may include a first sealing portion and a second sealing portion disposed outside the first sealing portion.

According to Aspect 13, in the electrode of Aspect 12, a modulus of elasticity of the first sealing portion may be greater than a modulus of elasticity of the second sealing portion.

According to Aspect 14, in the electrode of Aspect 12, a modulus of elasticity of the second sealing portion may be greater than a modulus of elasticity of the first sealing portion.

According to Aspect 15, in the electrode of Aspect 12, the first sealing portion may contain a porous material.

According to Aspect 16, in the electrode of Aspect 12, the liquid wire may contain a porous material.

The present disclosure includes appropriate combinations of any of the various embodiments and/or examples described above, and achieves advantageous effects of the corresponding embodiments and/or examples.

The electrode according to the present invention can reduce changes in resistance caused by surface changes, and can suppress noise in signals. The electrode described herein is useful when used as a biomedical electrode, or when used on a changing surface of a non-living object. For example, in application to living bodies, the electrode can be used as a biomedical electrode, whereas in application to non-living objects, the electrode can be used for IoT purposes.

What is claimed is:

1. An elastically deformable electrode comprising:
   a plurality of electrode elements spaced from each other; and
   a liquid wire electrically connecting the plurality of electrode elements,
   wherein, when the electrode is elastically deformed in such a way that a first distance between two of the plurality of electrode elements is twice a second distance between the two of the plurality of electrodes when not elastically deformed, a first resistance at the first distance is less than or equal to 50 times a second resistance at the second distance.

2. The electrode according to claim 1, wherein the plurality of electrode elements are disposed to form a first surface of the electrode.

3. The electrode according to claim 2, wherein the liquid wire contains a ferromagnetic material, and the electrode further comprises a magnet that overlaps at least one of the plurality of electrode elements in a plan view of the electrode, the magnet configured to attract the ferromagnetic material.

4. The electrode according to claim 1, wherein the liquid wire contains a metal which is liquid at ordinary temperature.

5. The electrode according to claim 1, wherein the liquid wire contains a metal containing greater than or equal to 60% by weight of gallium.

6. The electrode according to claim 5, wherein the liquid wire contains a metal containing less than or equal to 40% by weight of indium.

7. The electrode according to claim 1, wherein the liquid wire extends from a first toward a second of two adjacent electrodes of the plurality of electrode elements.

8. The electrode according to claim 1, further comprising a resin sealing the liquid wire.

9. The electrode according to claim 1, further comprising a substrate disposed so as to support the plurality of electrode elements.

10. The electrode according to claim 1, further comprising a sealing portion configured to seal the liquid wire.

11. The electrode according to claim 10, wherein the sealing portion includes a first sealing portion proximal to the liquid wire and a second sealing portion outside the first sealing portion.

12. The electrode according to claim 11, wherein a modulus of elasticity of the first sealing portion is greater than a modulus of elasticity of the second sealing portion.

13. The electrode according to claim 11, wherein a modulus of elasticity of the second sealing portion is greater than a modulus of elasticity of the first sealing portion.

14. The electrode according to claim 11, wherein the first sealing portion contains a porous material.

15. The electrode according to claim 1, wherein the liquid wire contains a porous material.

16. The electrode according to claim 1, further comprising a solid wire sealing the liquid wire.

17. The electrode according to claim 16, further comprising an insulator between the solid wire and the plurality of electrode elements.

18. The electrode according to claim 1, wherein the liquid wire comprises a matrix of a liquid resin and a conductive material dispersed in the matrix.

19. An elastically deformable electrode comprising:
a plurality of electrode elements spaced from each other; and
a liquid wire electrically connecting the plurality of electrode elements,
wherein, when the electrode is elastically deformed in such a way that a first distance between two of the plurality of electrode elements is twice a second distance between the two of the plurality of electrodes when not elastically deformed, a first resistance of the liquid wire connecting the two electrode elements at the first distance is less than or equal to 10 times a second resistance of the liquid wire connecting the two electrode elements at the second distance.

* * * * *